United States Patent [19]
Peters

[11] Patent Number: 6,016,195
[45] Date of Patent: Jan. 18, 2000

[54] FIBER OPTIC DEVICE FOR DETECTING THE SCATTERED LIGHT OR FLUORESCENT LIGHT FROM A SUSPENSION

[75] Inventor: Rainer Peters, Langen, Germany

[73] Assignee: ALV-Laser Vertriebsgesellschaft mbH, Langen, Germany

[21] Appl. No.: 09/094,777

[22] Filed: Jun. 15, 1998

[30] Foreign Application Priority Data

Jun. 15, 1997 [DE] Germany .............................. 197 25 211

[51] Int. Cl.[7] ................................................. G01N 21/00
[52] U.S. Cl. .......................... 356/342; 356/337; 356/73.1
[58] Field of Search .................... 356/342, 337, 356/73.1

[56] References Cited

U.S. PATENT DOCUMENTS

| | | | |
|---|---|---|---|
| 4,099,875 | 7/1978 | McMahon | 356/342 |
| 5,141,312 | 8/1992 | Thompson | 356/218 |

OTHER PUBLICATIONS

Wiese, H. and Horn, D., "Single–mode fibers in fiber–optic quasielastic light scattering: A study of the dynamics of concentrated latex dispersions", May 15, 1991, J. Chem. Phys. 94(10), American Institute of Physics, pp. 6429–6443.

Ansari, Rafat R. et al., "Microemulsion characterization by the use of a noninvasive backscatter fiber optic probe", Jul. 20, 1993, Applied Optics, vol. 32, No. 21, pp. 3822–3827.

Rogers, Richard B. et al., "A Compact Laser Light Scattering Instrument for Microgravity Research", 1996, Photon Correlation & Scattering, 1996 Technical Digest Series, vol. 14, pp. 40–42.

Rička, Jaroslav, "Dynamic light scattering with single–mode and multimode receivers", May 20, 1993, Applied Optics, vol. 32, No. 15, pp. 2860–2875.

*Primary Examiner*—Robert Kim
*Assistant Examiner*—Reginald Ratliff
*Attorney, Agent, or Firm*—Kenyon & Kenyon

[57] ABSTRACT

The present invention relates to a fiber optic detector for detection of scattered light or fluorescent light from a liquid suspension, comprising: a lighting optical fiber for transmitting light to a lighting optical fiber outlet; a first gradient index lens disposed at the lighting optical fiber outlet to parallelize light; a detecting optical fiber for transmitting back-scattered light from a detecting optical fiber inlet; a second gradient index lens disposed at the detecting optical fiber inlet to parallelize back-scattered light; and at least one means for focusing parallelized light transmitted from the lighting optical fiber on a point and for focusing light back-scattered from the point to the second gradient index lens of the detecting optical fiber for transmission by the detecting optical fiber.

20 Claims, 3 Drawing Sheets

FIBER OPTIC DEVICE FOR DETECTING THE SCATTERED LIGHT OR FLUORESCENT LIGHT FROM A SUSPENSION

FIELD OF THE INVENTION

The present invention relates to a fiber optic device for detecting the scattered light or fluorescent light of a suspension.

RELATED TECHNOLOGY

Fiber optic detectors may be used for detecting the intensity of scattered light (static light scattering) and the fluctuations of scattered light (dynamic light scattering) occurring due to particle diffusion in a solvent.

Basically, fiber optic detectors can be divided into three categories:

Detectors whose main advantage consists in their compact design compared to conventional detectors, see Photon Correlation & Scattering, Aug. 21–24, 1996, Capri, Italy, in 1996 Technical Digest Series, Vol. 14, Optical Society America, pp. 23–25 and pp. 40–42;

Detectors whose main advantage consists in the scattered light mode selection and thus improved signal/noise ratio for dynamic light scattering, see J. Ricka, Dynamic Light Scattering with Single-mode and Multimode Receivers, Applied Optics 32, 2860–2875 (1993), hereby incorporated by reference; and Detectors whose main advantage consists of their improved ability to measure highly concentrated, absorbent, and highly concentrated and absorbent suspensions.

Detectors in the prior art used for measuring scattered or fluorescent light in highly concentrated suspensions can be divided into two main groups:

Invasive fiber optic detectors that allow measurements to be made by direct immersion into the suspension (Wiese H. and Horn D., "Single-mode fibers in fibre-optic quasielastic light scattering: A study of the dynamics of concentrated latex dispersions," J. Chem. Phys., Vol. 94, No. 10, May 15, 1991, pp. 6429–6443) and Non-invasive fiber optic detectors that allow measurement in a cell or through a glass window (Ansari R. R., Dhadwal H. S., Cheung H. M., Meyer W. V., "Microemulsion characterization by the use of a non-invasive backscatter fiber optic probe," Applied Optics, Vol. 32, No. 21, p. 3822–3823, Jul. 20, 1993). This article by Ansari et al. is hereby incorporated by reference.

In order to allow high particle concentrations to be measured, these known detectors must ensure that multiple scattering is suppressed. This can be achieved by selecting a scattering angle close to 180° and using very small actual or apparent scattering volumes, the latter through mode selection. Results of such measurements are highly dependent on the suppression of multiple scattering because particle concentrations of less than 10 vol. % seldom occur in these measurements.

Further, the dynamic light scattering cannot be measured without suppression of multiple scattering.

Only such measurement method known as Diffusing Wave Spectroscopy is measurement of pure multiple scattering used to obtain information about the average particle size.

In contrast, with the fiber optic device according to this invention and with the instrument equipped therewith, light scattering can only be measured both on concentrated suspensions and highly diluted suspensions.

The invasive fiber optic detectors known in the prior art can be industrially used to monitor polymerization. However, the known detectors have two serious disadvantages: 1) The expected operating time in a concentrated suspension is short due to the clogging of the fiber by deposits from the suspension, and 2) The back-reflection of the laser light at the fiber outlet is disturbing when operating with less than extremely high concentrated suspensions because the intensity of the reflection may amount to several times that of the scattered light. The problem of the back-reflection can be alleviated by an appropriate finish, i.e., polishing, of the fiber outlet end. The problem of back-reflection is not completely solved however, because even the most favorable case of 50 nW reflection intensity provides a sub-pW scattering intensity at too low a concentration as compared to a 50 $\mu$W laser intensity at the fiber outlet end. (For the purposes of this specification, $\mu=1\times10^{-6}$). The problem of fiber clogging due to the suspension deposits at the fiber outlet cannot be fully controlled in the invasive technique.

The invasive detector known in the art, by its very design, is ill-suited for measuring either multiple scattering or fluctuations of the number of particles. Because of the unrestricted mode selection, there is an inherent difficulty of excessive back-reflection if back-scattering multiple-scattered light into the fiber.

The noninvasive detectors known in the prior art disadvantageously have a high divergence of the exiting light. For a numerical aperture of 0.1, a working distance of more than about 1 mm and a scattering angle of 143°, a beam diameter of 300 $\mu$m results on the inside of the cell and roughly 1 mm at the end of the overlapping volume. The optical attenuation in the cell due to the strong divergence of the beam strongly depends on the cell geometry, so that optimization for round or rectangular cells is indispensable. As the working distance becomes larger, the beam radius becomes larger. As the beam radius becomes larger, the back-scattered light, a function of photon density, becomes weaker. Accordingly, larger working distances are not recommended with such noninvasive fiber optic detectors.

In the case of dynamic measurements, the known noninvasive fiber detector described cannot measure the fluctuation in the number of particles because of the excessive scattering volume. In this case, the condition that no more than 10 particles can be present in the scattering volume cannot be ensured. Further, a high photon density cannot be maintained in the scattering volume with the known noninvasive detector. The noninvasive fiber optic detector appears to be basically appropriate for multiple scattering measurements except for the problem of the poorly defined scattering angle. Practical applications for such noninvasive detectors are not generally known.

OBJECTS AND SUMMARY OF THE INVENTION

The present invention provides a fiber optic device whose main advantage consists in its improved ability to measure highly concentrated and/or absorbent suspensions. The present invention has the advantage of an expanded concentration range, almost complete suppression of multiple scattering, and a large range of effective desired working distance between the detector and a sample. These advantages allow the device to be used in environments where dynamic light scattering measurement was previously difficult if not completely impossible, i.e., in industrial production systems and process monitoring. The fiber optic device according to this invention is also well-suited for other measurement applications such as the measurement of multiple scattering and the measurement of fluctuations in the number of particles.

Another object of the present invention is to combine the advantages of a non-invasive fiber optic detector with those of an invasive fiber optic detector, i.e., high photon density at a wide range of effective working distances with a scattering angle up to about 180°.

Another object of the present invention is achieved by a fiber optic device for detection of any scattered light and fluorescent light from a liquid suspension with the following features:

- a lighting optical fiber for transmitting light to a lighting optical fiber outlet;
- a first gradient index lens disposed at the lighting optical fiber outlet for parallelizing light;
- a detecting optical fiber for transmitting back-scattered light from a detecting optical fiber inlet to a detecting optical fiber outlet;
- a second gradient index lens disposed at the detecting optical fiber inlet to parallelize back-scattered light; and
- at least one means for focusing parallelized light transmitted from the lighting optical fiber on a point and for focusing light back-scattered from the point to the second gradient index lens of the detecting optical fiber for transmission by the detecting optical fiber.

By using fibers with substantially identical optical characteristics in lighting and detection, optimum detection of scattered light is made possible, i.e., the use of single-mode or few-mode fibers, i.e., those having a conduction characteristic of three to ten modes, is recommended. If detection were in the same plane as lighting, i.e., in the planes of the X and Y axes, a cofocal arrangement would be obtained, as is the case of an invasive detector with a scattering angle of 180°. However, since the device is installed slightly shifted in one plane, a somewhat smaller scattering angle is obtained.

The advantages of the present invention as compared with the detectors of the known related art are the following:

- Back-reflection does not generally occur, since lighting and detection are strictly separated in space;
- The very small beam diameter of the lighting and detecting optical fibers, on the order of 50 to 100 $\mu$m, guarantees that the beam shape does not strongly depend on the cell geometry; this means that round or rectangular cells can be used interchangeably, and the measurement results are not affected by the resulting different window wall thicknesses;
- Very high photon densities can be achieved by focused lighting and detection;
- Scattering angles very close to 180° are possible; in practice, a scattering angle of 172.9° has been tested with 5-mm fiber separation and 40-mm focal length of the lens, as well as a scattering angle of 176.4° with 5-mm fiber separation and 80-mm focal length of the lens;
- The working distance can be freely selected due to the use of lenses of different focal lengths.

Another advantage of the fiber optic device according to the present invention is that it can be modified, by adding more detecting optical fibers, so that it encompasses a scattering angle range of up to about 135°. In this case, however, a superior quality lens system and a 1:1 aperture are then needed.

The fiber optic device according to the present invention and an instrument equipped therewith can also be used for measuring the fluctuation in the number of particles with the help of scattering light measurement or fluorescent light measurement. The particle concentration in the measured volume is so small that the number of particles in the volume is statistically no longer constant, but has a high degree of variance. With the invention herewith disclosed, the number and diffusion coefficient of the particles are determined by analyzing the variance in scattered light at natural or forced fluorescence. The analysis of the dynamic light scattering fails here because the required 1000 particles present in the volume is not met. Measuring the fluctuation in the number of particles requires a minimum possible illuminated volume in order to have larger variances. This is accomplished by selecting a lens or a lens system with the smallest possible focal length. For a 10 mm lens focal length, the theoretical size of the focal point is reduced to approximately 8–10 $\mu$m. For a 5 mm lens focal length, a focal point size of 4–5 $\mu$m is achieved.

Because only the variation of the overall scattered or fluorescent light in the scattering volume over time is of interest, all detecting optical fibers can be connected to a single-photon counter, and no mode selection by the detecting optical fibers needs to take place. This means that single-mode, few-mode, and multimode optical fibers can equally be used according to the present invention. The use of single-mode or few-mode optical fibers is preferred. Also, a plurality of photon counters and detecting optical fibers may be used according to the present invention.

For fluorescent light measurements, a filter must be provided that lets the fluorescent light through, but filters out the primary excitation light. This filter is placed upstream from the single-photon counter.

The multiple application possibilities of the fiber optic device according to the present invention and an instrument equipped therewith are illustrated when the fiber optic device is used for measuring multiple scattering. In this measurement method, the light subjected to multiple scattering, i.e., light scattered several times on one or more particles in the same or different directions and the statistically unique characteristics of the light that has undergone multiple scattering are studied. For this purpose, a device is needed that provides no suppression of multiple scattering. The fiber optic device according to the present invention satisfies this purpose by providing detection of scattered light far beyond the focal point. In this case only light that has undergone multiple scattering enters the detecting optical fiber. When a lens with a large focal length is used, the scattering angle may be close to 180°. This satisfies the requirement of multiple scattering that the scattering angle (transmission measurement) be 180° or 0°.

BRIEF DESCRIPTION OF THE DRAWINGS

In the following, the prior art (FIGS. 1–2) and the present invention (FIGS. 3–8) are explained in more detail with the aid of drawings.

DETAILED DESCRIPTION

Figure 1:
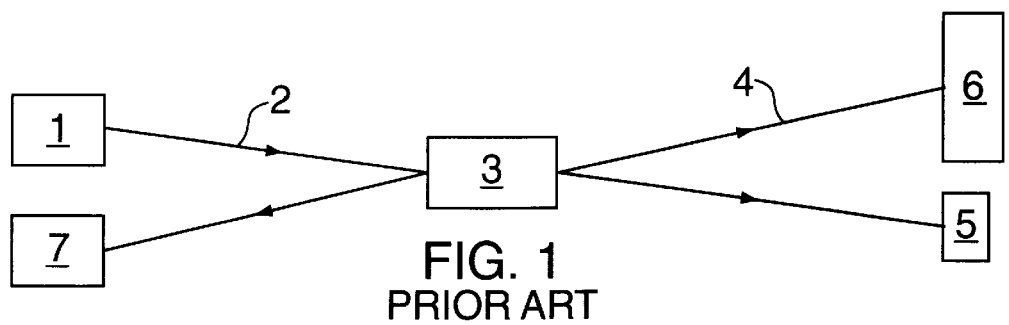
FIG. 1 illustrates an embodiment in the prior art of an invasive fiber optic detector.

FIG. 1 illustrates a conventional "invasive" fiber optic detector, in which a beam emitted by a laser 1 is split using a single-mode optical fiber 2 via a fiber optic beam splitter 3 and one fiber end 4 (lighting/detection fiber) is directly immersed in the suspension after splitting.

The laser beam is usually split in the proportion 5%:95% in order to allow detection of the scattered light with minimum loss. This means that 5% of the laser beam is introduced in the suspension, while the remaining 95% is extinguished in beam trap 5 at the second fiber end. The light scattered back from the suspension into cell 6, which is scattered back into optical fiber 4 with a scattering angle of about 180°, goes in the opposite direction, reaches beam splitter 3 and 95% of the light scattered back is injected in photodetector 7, e.g., a single-photon counter.

Figure 2:
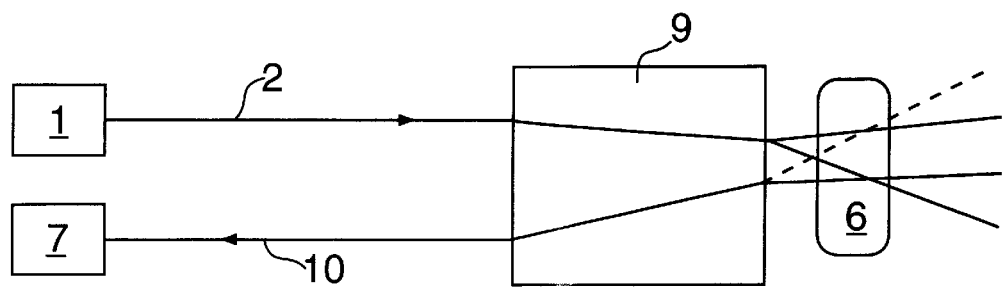
FIG. 2 illustrates an embodiment in the prior art of a noninvasive detector.

FIG. 2 illustrates a conventional "non-invasive" fiber optic detector. The beam emitted by laser 1 is transmitted via a single-mode lighting optical fiber 2 and a mechanical guide 9. A detecting optical fiber 10, is directed onto cell 6 using the same mechanical guide 9. The lighting optical fiber 2 and the detecting optical fiber 10 have substantially similar optical characteristics and typically are single-mode fibers with a numerical aperture of approximately 0.1. This results in an overlapping scattering volume for the two fibers at a certain distance and at a certain angle. Only light from this scattering volume can penetrate detecting optical fiber 10 and be guided onto photodetector 7.

The arrangement of the lighting optical fiber 2 and detecting optical fiber 10 in relation to one another depends on the desired working distance, the glass thickness of cell 6 and other variables. Typical commercially available arrangements are optimized for a glass thickness of less than 1 mm and a working distance of somewhat over 1 mm. This results in an optimum scattering angle of approx. 143°, i.e., substantially less than 180° and therefore not optimum for suppressing multiple scattering.

Figure 3:
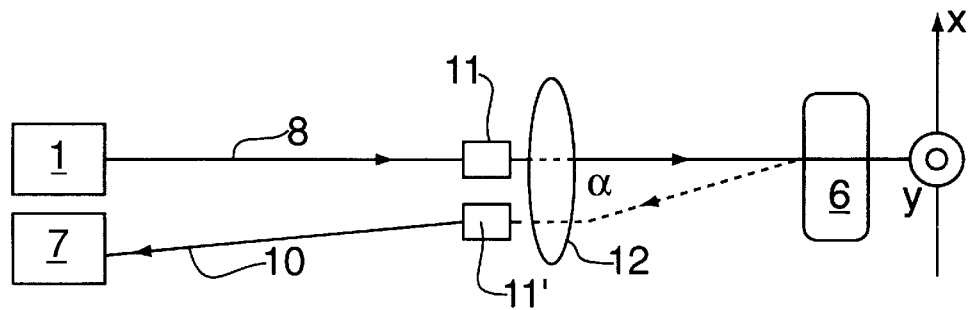
FIG. 3 illustrates an embodiment of the present invention of a fiber optic device.

FIG. 3 illustrates an embodiment of the present invention of a fiber optic device having a scattering angle close to 180°. In FIG. 3, the laser beam generated by laser 1 is focused on cell 6 by a lighting optical fiber 8 with a gradient index lens 11 at a fiber outlet of the lighting optical fiber 8 through a lens or a lens system 12. The lighting optical fiber 8 can be a single-mode fiber, a polarization-preserving single-mode fiber or a polarizing single-mode fiber. Such fibers are commercially available from Wave Optics, USA. At the fiber outlet of lighting optical fiber 8, a parallel beam with Gaussian beam profile and optimum focusability can be obtained. The size of the focus of the laser 1 is in part dependent on the inlet aperture of the laser 1 after exiting from the lighting optical fiber 8 and upon reaching the lens 12, on the lens focal length and the light wavelength, i.e., it is diffraction-limited. Likewise, a detecting optical fiber 10 is installed so that it transmits scattered light to photodetector 7 through the lens 12 at a scattering angle a using a gradient index lens 11'.

Figure 4:
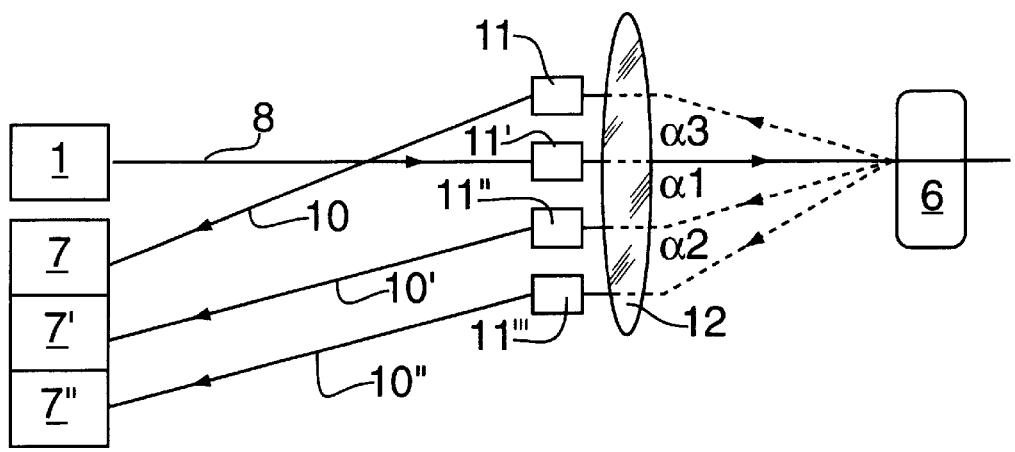
FIG. 4 illustrates another embodiment of the present invention having a plurality of detecting optical fibers which forward scattered light to a photodetector.

In FIG. 4, the laser beam produced by laser 1 is focused on cell 6 through lighting optical fiber 8 and gradient index lens 11' and then through lens or lens system 12. Scattered light is focused by lens or lens system 12 at scattering angles $a_1$, $a_2$, $a_3$, parallelized by gradient index lenses 11, 11", 11"', and transmitted by a plurality of detecting optical fibers 10, 10', 10" to photodetectors 7, 7', 7".

Figure 5:
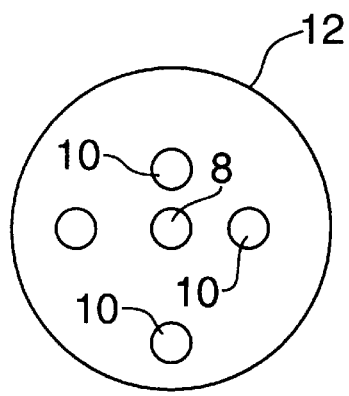
FIG. 5 illustrates a front view similar to FIG. 4 as observed through a lens or lens system.

FIG. 5 illustrates a front view similar to FIG. 4 through the lens or lens system 12 with a central lighting optical fiber 8 and a plurality of detecting optical fibers 10, 10', 10" arranged in any desired manner.

Figure 6:
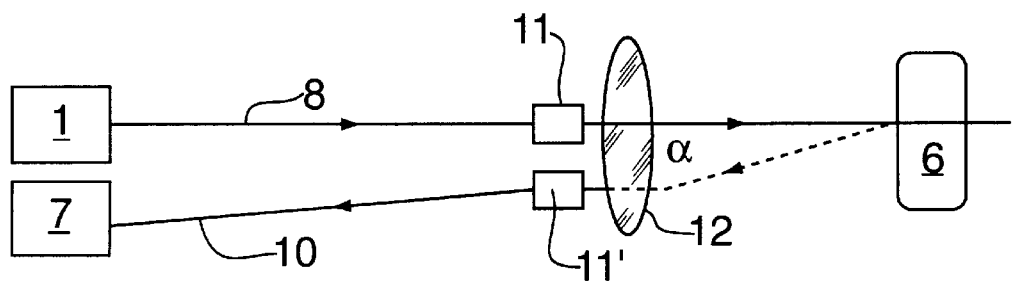
FIG. 6 illustrates another embodiment of the present invention having a lens with a relatively large focal length.

FIG. 6 illustrates an embodiment of the present invention wherein a lens 12 with a relatively large focal length, about 80 mm, is used. This embodiment necessitates a much greater distance between the cell 6 and the detector 7 in order to measure multiple scattering with angle α of about 180° multiple scattering. No other optical modifications are needed.

Figure 7:
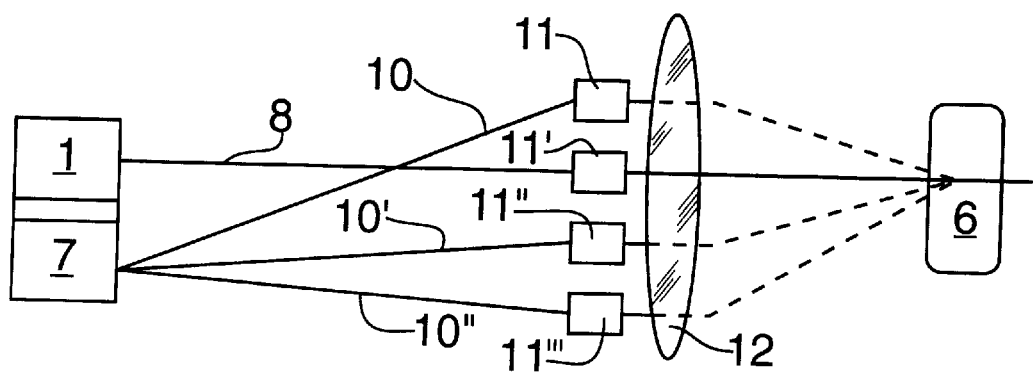
FIG. 7 illustrates another embodiment of the present invention wherein a plurality of detecting optical fibers are distributed in a circle around the lighting optical fiber.

FIG. 7 illustrates an embodiment of the present invention wherein a plurality of detecting optical fibers 10, 10', 10" having gradient index lenses 11,11",l1"' are distributed preferably in a circle around the lighting optical fiber 8, having gradient index lens 11', to increase the sensitivity to scattered light in the event that very few particles are present. In this embodiment, each detecting optical fiber 10, 10', 10" is connected to a separate detector 7, 7', 7".

Figure 8:
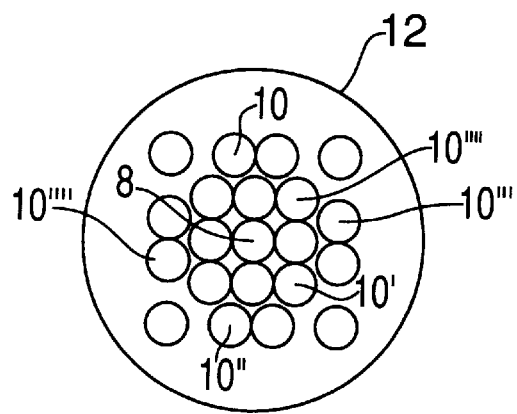
FIG. 8 illustrates a front view similar to FIG. 7 as observed through a lens or lens system.

FIG. 8 illustrates a front view through lens or lens system 12 similar to FIG. 7 showing the central location of lighting optical fiber 8 and the surrounding detecting optical fibers 10,10', 10", 10"', 10"", 10""'.

What is claimed is:

1. A fiber optic device for detection of scattered light or fluorescent light from a suspension, comprising:
    a lighting optical fiber for transmitting light to a lighting optical fiber outlet;
    a first gradient index lens disposed at the lighting optical fiber outlet for parallelizing light;
    a detecting optical fiber for transmitting back-scattered light from a detecting optical fiber inlet to a detecting optical fiber outlet;
    a second gradient index lens disposed at the detecting optical fiber inlet to parallelize back-scattered light; and
    at least one means for focusing parallelized light transmitted from the lighting optical fiber on a point and for focusing light back-scattered from the point to the second gradient index lens of the detecting optical fiber for transmission by the detecting optical fiber.

2. The device of claim 1 wherein the means for focusing comprises at least one lens.

3. The device of claim 2 wherein the lighting optical fiber is a fiber selected from the group consisting of a single-mode fiber; a polarization-preserving single-mode fiber; a polarizing single-mode fiber.

4. The device of claim 2 wherein the means for focusing has a focal length in the range of about 40 mm to about 80 mm.

5. The device of claim 2 wherein the means for focusing has an aperture of 0.1.

6. The device of claim 2 further comprising a plurality of detecting optical fibers wherein each detecting optical fiber is associated with a separate gradient index lens.

7. The device of claim 6, wherein the plurality of detecting optical fibers are arranged in a circular pattern around the lighting optical fiber.

8. The device of claim 3 wherein the lighting optical fiber and the detecting optical fiber are single-mode fibers.

9. The device of claim 1 wherein the lighting optical fiber and the detecting optical fiber have a beam diameter in the range of about 50 to about 100 µm.

10. The device of claim 2 wherein an optical fiber separation is about 5 mm, a focal length of the means for focusing is about 40 mm, and a scattering angle, α, is about 172.9°.

11. The device of claim 2 wherein an optical fiber separation is about 5 mm, a focal length of the means for focusing is about 80 mm, and a scattering angle, α, is about 176.4°.

12. The device of claim 2 wherein the detecting optical fiber is a fiber selected from the group consisting of a single-mode optical fiber and a multimode optical fiber.

13. The device of claim 12 wherein the detecting optical fiber is a fiber selected from the group consisting of a 3-mode optical fiber, 4-mode optical fiber, 5-mode optical fiber, 6-mode optical fiber, 7-mode optical fiber, 8-mode optical fiber, 9-mode optical fiber, and 10-mode optical fiber.

14. The device of claim 1 further comprising a means for detecting light connected to the detecting optical fiber outlet.

15. The device of claim 14 wherein the means for detecting light is a photon counter.

16. The device of claim 14 further comprising a plurality of detecting optical fibers wherein each detecting optical fiber is connected to a separate means for detecting.

17. The device of claim 14, further comprising a filter means for absorbing a primary excitation light in back-scattered light disposed upstream from the means for detecting light.

18. A method for measuring scattered light using the device of claim 1.

19. A method for manufacturing a device of claim 2, comprising the steps of:

provviding a lighting optical fiber for transmitting light to a lighting optical fiber outlet;

transmitting back-scattered light with a detecting optical fiber from a detecting optical fiber inlet to a detecting optical fiber outlet;

disposing a first gradient index lens at the lighting optical fiber for parallelizing transmitted light disposing a second gradient index lens at the detecting optical fiber for parallelizing back-scattered light; and providing at least one means for focusing parallelized light transmitted from the lighting optical fiber on a point and for focusing back-scattered light from the point to the second gradient index lens for transmission by the detecting optical fiber.

20. A method for manufacturing a fiber optic device for detection of scattered light or fluorescent light from a liquid suspension, comprising the steps of:

providing a lighting optical fiber for transmitting light to a lighting optical fiber outlet;

disposing a first gradient index lens at the lighting optical fiber outlet for parallelizing transmitted light;

transmitting back-scattered light through a detecting optical fiber from a detecting optical fiber inlet to a detecting optical fiber outlet;

disposing a second gradient index lens at the detecting optical fiber inlet for parallelizing back-scattered light; and providing a means for focusing parallelized light transmitted from the lighting optical fiber on a point and for focusing back-scattered light from the point to the second gradient index lens for transmission by the detecting optical fiber.

* * * * *

UNITED STATES PATENT AND TRADEMARK OFFICE
CERTIFICATE OF CORRECTION

PATENT NO. : 6,016,195
DATED : January 18, 2000
INVENTOR(S) : Rainer Peters

Page 1 of 1

It is certified that error appears in the above-identified patent and that said Letters Patent is hereby corrected as shown below:

Column 5,
Line 67, "a" (2nd occurrence) should be -- $\alpha$ --; and

Column 6,
Line 5, "$a_1$, $a_2$, $a_3$" should be -- $\alpha_1$, $\alpha_2$, $\alpha_3$ --.

Signed and Sealed this

Thirty-first Day of July, 2001

Attest:

NICHOLAS P. GODICI
Attesting Officer
Acting Director of the United States Patent and Trademark Office